United States Patent [19]
Dehlinger

[11] Patent Number: 5,759,779
[45] Date of Patent: Jun. 2, 1998

[54] POLYNUCLEOTIDE-ARRAY ASSAY AND METHODS

[76] Inventor: Peter J. Dehlinger, 58 Roosevelt Cir., Palo Alto, Calif. 94306

[21] Appl. No.: 585,365

[22] Filed: Jan. 11, 1996

Related U.S. Application Data

[63] Continuation-in-part of Ser. No. 563,179, Nov. 27, 1995, and a continuation-in-part of Ser. No. 520,730, Aug. 29, 1995.

[51] Int. Cl.⁶ .................. C12Q 1/68; C12P 19/34; C07H 21/04; C07H 21/02
[52] U.S. Cl. .................. 435/6; 435/5; 435/91.1; 435/91.2; 436/501; 436/543; 436/518; 436/7.1; 536/18.5; 536/25.3; 536/23.1; 536/24.3; 530/333; 530/334
[58] Field of Search .................. 435/6, 5, 91.2, 435/91.1, 174; 536/24.3–24.33, 18.5, 25.3, 23.1; 436/518, 7.1, 501, 543; 530/333, 334

[56] References Cited

U.S. PATENT DOCUMENTS

| | | |
|---|---|---|
| 4,371,273 | 2/1983 | Kendall et al. |
| 4,576,477 | 3/1986 | Corbet et al. |
| 4,683,202 | 7/1987 | Mullis. |
| 5,143,854 | 9/1992 | Pirrung et al. |
| 5,212,979 | 5/1993 | Albrodt et al. |
| 5,274,240 | 12/1993 | Mathies et al. |
| 5,391,785 | 2/1995 | Jones et al. |
| 5,439,578 | 8/1995 | Dovichi et al. |
| 5,449,754 | 9/1995 | Nishioka. |
| 5,503,980 | 4/1996 | Cantor ............... 435/6 |

FOREIGN PATENT DOCUMENTS

| | | |
|---|---|---|
| 0 373 203 B1 | 8/1994 | European Pat. Off. |
| WO 94/11530 | 5/1994 | WIPO ............... 435/6 |
| WO 94/27719 | 12/1994 | WIPO. |
| WO 95/11262 | 4/1995 | WIPO. |
| WO 96/33010 | 10/1996 | WIPO. |

OTHER PUBLICATIONS

Bunin, B.A., and Ellman, J.A., "A General and Expedient Method for the Solid Phase Synthesis of 1,4-Benzodiazepine Derivatives," *J. Am. Chem. Soc.* 114:10997–10998 (1992).

Bunin, B.A., et al., "The Combinatorial Synthesis and Chemical and Biological Evaluation of a 1,4-Benzodiazepine Library," *Proc. Natl. Acad. Sci. USA* 91:4708–4712 (1994).

DeWitt, S.H., et al., "'Diversomers': An Approach to Nonpeptide, Nonoligomeric Chemical Diversity," *Proc. Natl. Acad. Sci. USA* 90:6909–6913 (1993).

Fodor, S.P.A., et al., "Light-Directed, Spatially Addressable Parallel Chemical Synthesis," *Science* 251:767–773 (1991).

Geysen, H.M., et al., "Use of Peptide Synthesis to Probe Viral Antigens for Epitopes to a Resolution of a Single Amino Acid," *Proc. Natl. Acad. Sci. USA* 81:3998–4002 (1984).

*Primary Examiner*—W. Gary Jones
*Assistant Examiner*—Dianne Rees
*Attorney, Agent, or Firm*—Dehlinger & Associates

[57] ABSTRACT

A method of analyzing the sequence of a polynucleotide analyte. The method includes contacting the analyte with a position-addressable array of oligonucleotides, each anchored to a solid support and having a 5'proximal and 3'-distal orientation. The hybridized oligonucleotides are then extended by strand-directed polymerase, to produce labeled, extended oligonucleotides at positions of the array corresponding to sequence matches between the array oligonucleotides and analyte regions. The pattern of label in the array is used to analyze analyte sequence.

7 Claims, 6 Drawing Sheets

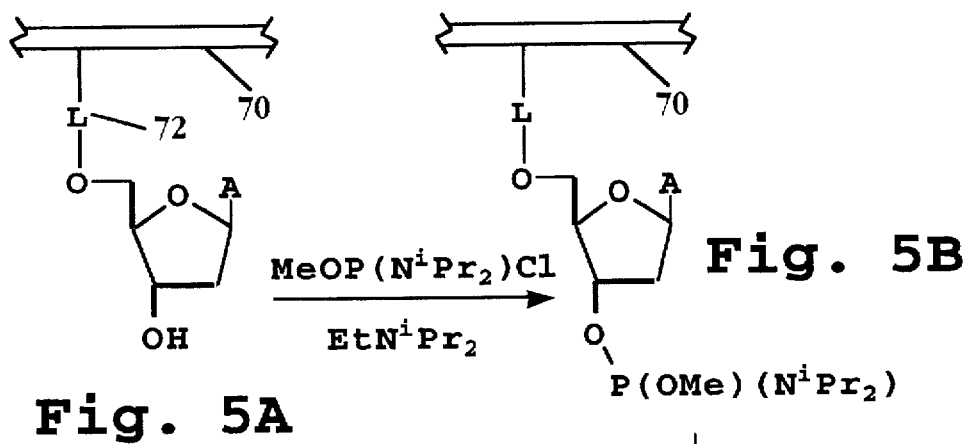
Fig. 5A
Fig. 5B
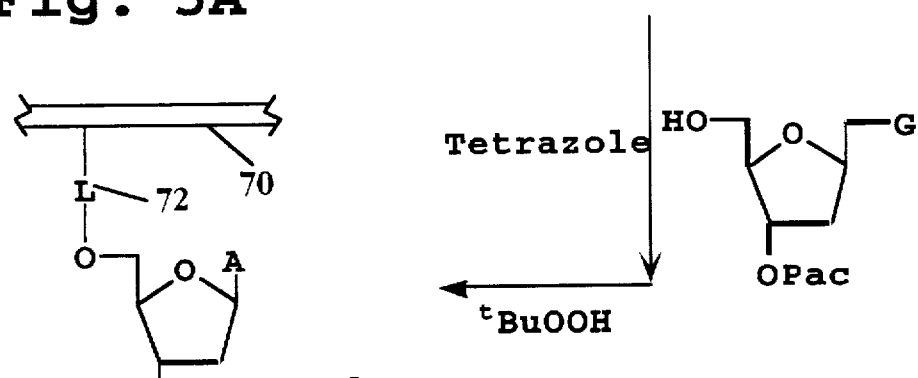
Fig. 5C
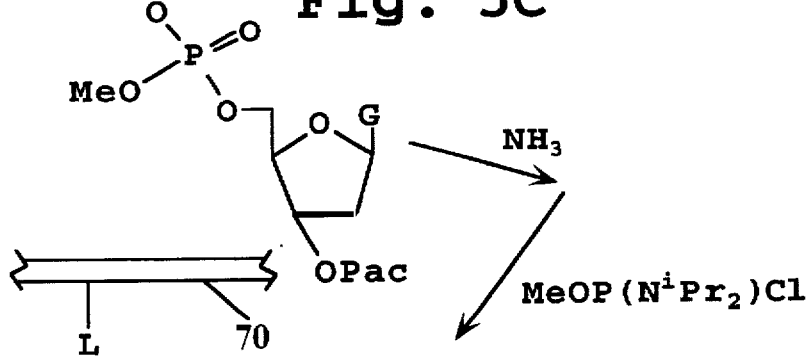
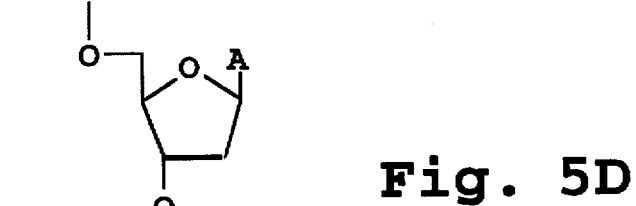
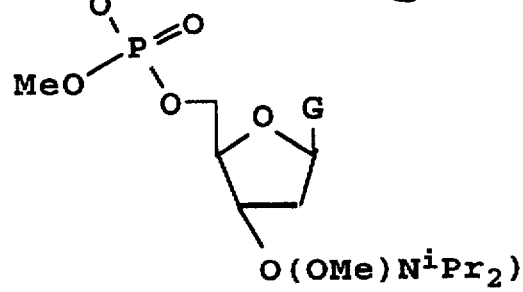
Fig. 5D

```
                    (G)
       ...ATTCGAGATCGACTTACT...          Fig. 7A

TAAGCTCT
         AAGCTCTA
          AGCTCTAG          Fig. 7B
           GCTCTAGC
            CTCTAGCT
             TCTAGCTG
              CTAGCTGA
               TAGCTGAA
                AGCTGAAT
                 GCTGAATG
                  CTGAATGA

TAAGCTCT
         AAGCTCTC
          AGCTCTCG
           GCTCTCGC
            CTCTCGCT       Fig. 7C
             TCTCGCTG
              CTCGCTGA
               TCGCTGAA
                CGCTGAAT
                 GCTGAATG
                  CTGAATGA
```

POLYNUCLEOTIDE-ARRAY ASSAY AND METHODS

This application is a continuation-in-part of U.S. patent application Ser. No. 08/563,179 for "Method and Apparatus for Producing Position-Addressable Combinatorial Libraries", filed Nov. 27, 1995, and U.S. patent application Ser. No. 08/520,730 "Position-Addressable Polynucleotide Arrays", filed Aug. 29, 1995. These applications are incorporated herein by reference.

FIELD OF THE INVENTION

The present invention relates to a method for generating a position-addressable polynucleotide array, and assays that use the array.

REFERENCES

Drmanac, et al., *Science* 260:1649–1652 (1993).
Eichler, J., et al., *Biochemistry* 32(41):11035 (1993).
Felder, E. et al., PCT Intl. Appn. Pubn. No. WO 9516209 (6/1995).
Fodor, S. P. A., et al., *Science* 251:767–773 (1991).
Fodor, S. P. A., et al., PCT Application WO 95/00530, published January, 1995.
Furka, A., et al., *Int. J. Pept. Protein Res.* 37:487–493 (1991).
Gait, M. J., Ed., *OLIGONUCLEOTIDE SYNTHESIS: A PRACTICAL APPROACH*, Oxford University Press, Oxford, UK (1990).
Geysen, H. M., et al., *Proc. Natl. Acad. Sci. USA* 81:3998–4002 (1984).
Geysen, H. M., et al., *Proc. Natl. Acad. Sci. USA* 82:178–182 (1985).
Hames, B. D., et al., *NUCLEIC ACID HYBRIDIZATION*, IRL Press (1985).
Houghten, R. A., et al., *Nature* 354:84–86 (1991).
Houghten, R. A., et al., *BioTechniques* 13:412–421 (1992).
Kramer, A., et al., *Pept. Res.* 6(6):314 (1993).
Matson, R. S. et al., *Anal. Biochem.* 217, 306–310 (1994).
Matson, R. S. et al., *Anal. Biochem.* 224, 110–116 (1995).
Nestler, H. P. et al., *J. Org. Chem.* 59:4723–4724 (1994).
Pham, E. K. et al., PCT Intl. Appn. Pubn. No. WO 9513538 (5/1995).
Pinilla, C., et al., *Biotechniques* 13(6):901 (1992).
Pinilla, C., et al., *Gene* 128(1):71 (1993).
Pirrung, et al., U.S. Pat. No. 5,143,854 (1992).
Sambrook, J., et al., *MOLECULAR CLONING: A LABORATORY MANUAL*, Cold Spring Harbor Press, Cold Spring Harbor, N.Y. (1989).
Southern, E., EP Patent No. 373,203 (1994)
Southern, E. et al., *Genomics* 13:1008–1017 (1992).
Virnekas, B., et al., *Nuc. Acids Res.* 22(25):5600 (1994).

BACKGROUND OF THE INVENTION

There is widespread interest in oligonucleotide and gene arrays, for example, for use in gene-based diagnostics aimed at detecting one of a number of possible mutations in a given gene, and for sequencing-by-hybridization (SBH).

Heretofore, arrays of genes, e.g., cDNAs or genomic library clones, have been formed by spotting individual genes on suitable substrates, e.g., nitrocellulose filter paper, for subsequent blotting, e.g., with radiolabeled probes. This approach is relatively labor-intensive, requiring that each gene be individually spotted on the substrate. The approach is also limited in array-region density to the physical resolution achievable by the device used for spotting.

More recently, a method for preparation of high density position-addressable oligomer arrays on a planar substrate has been reported (Fodor, Pirrung). In this method a substrate having photoprotective groups is irradiated in selected regions only, using photolithographic mask techniques, to deprotect surface active groups in those selected regions. The entire surface is then treated with a solution of a selected subunit, which itself has a photoprotected group, to react this subunit with the surface groups in the photodeprotected regions. This process is repeated to (i) add a selected subunit at each region of the surface, and (ii) build up different-sequence oligomers at known, addressable regions of the surface.

This method has the advantage that reaction sites do not have to be physically separated during subunit addition, and therefore massive parallel subunit addition is possible by applying subunit-addition reagents over the entire surface of the array. Greater site density is therefore feasible than in systems where physical separation of reagents is required from one reaction site to another, and where individual reagents are spotted or deposited in defined array regions.

Co-pending application for Method and Apparatus for Producing Position-Addressable Combinatorial Libraries, filed Nov. 27, 1995, discloses another method for producing position-addressable, high-density arrays of oligomers. The approach involves drawing reaction solution sequentially into different selected subsets of capillary tubes, to add a subunit or substituent to the nascent library molecules in those tubes.

The method allows massive parallel subunit synthesis to efficiently produce high-density arrays of position-addressable oligomers, e.g., oligonucleotides. Thus, for example, to form a hexamer array of $4^6$ oligonucleotides, only four addition reactions are required at each subunit addition step (one for each of the four nucleotides), so that the total $4^6$ array can be produced in 4×6=24 reactions. By contrast, if each subunit were added separately to each array region, a total of $4^6$ separate subunit addition steps would be required (as, for example, proposed by Southern).

The direct use of massive parallel subunit addition, for synthesis of position-addressable oligomer libraries, is not, however, readily adaptable to the synthesis of position-addressable gene arrays for two reasons. First, since the gene sequences are expected to be random rather than combinatorial, there is no simple way of patterning the genes on a substrate so that the unique gene sequences can be built up by massive parallel step-wise synthesis. Secondly, good gene-sequence fidelity would be obtainable in high-density arrays only up to about 6–10 subunits, whereas genes or gene probes of interest will typically contain 15–100 or more nucleotides.

Parent application Ser. No. 08/520,730 for "Position-Addressable Polynucleotide Array", filed Aug. 29, 1995 discloses a method for converting a high-density, position-addressable, oligonucleotide-permutations library to a high-density polynucleotide array. The method includes contacting an array of different-sequence oligos having a unique, known combinatorial sequence associated with each position in the array with a set of extended gene probe templates which are complementary to the oligos at one of the template end regions. After hybridization, the oligos in the array are extended by strand-directed polymerization to form the probe array.

The present application discloses assay methods which employ oligonucleotide arrays of the type considered in the above co-pending patent applications.

SUMMARY OF THE INVENTION

The invention includes a method of analyzing a polynucleotide analyte sequence. The method involves first contacting the analyte with a position-addressable array of oligos (oligonucleotides), each anchored to a solid support and having a 5'-proximal and 3'-distal orientation. The contacting is carried out under conditions that allow hybridization of the analyte, with such in single-stranded form, to array oligos whose sequences are complementary to sequences within the analyte.

The analyte-hybridized array oligos are then extended by strand-directed polymerization, along analyte segments extending distal to the 3' ends of the hybridized array oligos, to produce extended oligos. The extending may be carried out in the presence of a reporter-labeled nucleotide triphosphate, such that the extended oligos contain one or more reporter-labeled nucleotide subunits. Alternatively, extended oligos, with such in double stranded form, may be labeled after oligo extension by introduction of a detectable duplex intercalating agent, such as ethidium bromide. The analyte sequence is then analyzed from the observed pattern of labeled, extended oligos in the array.

In one general embodiment, the reporter-labeled nucleotide triphosphate is a ligand-derivatized nucleotide, such as biotinylated nucleotide. The analyzing step is carried out by binding detectable-reporter anti-ligand, such as avidin or streptavidin, to the extended oligos, then detecting the pattern of anti-ligand label in the array.

In another general embodiment, the reporter-labeled nucleotide triphosphate is a fluorescent-labeled nucleotide, where the analyzing step is carried out by detecting the pattern of fluorescence emission in the array.

For all labeling methods, the method may further include measuring the level of fluorescence emission associated with different extended oligos in the array.

Where the method is used for analyzing the presence or absence of a sequence mutation at a given position in the analyte, the analyzing step includes comparing the observed pattern of extended, labeled oligos in the array with that expected for an analyte sequence having a known sequence at the position of the mutation.

Where the method is used for determining the sequence of the analyte, the oligo array is composed of oligos having a selected length of at least 8 subunits, and substantially all sequence permutations of oligos of that length are represented in the array. The analyzing step includes (i) determining the pattern of extended oligos in the array, and (ii) reconstructing an analyte sequence from the sequence overlap in the determined pattern. This may be done, for example, using a genetic algorithm which scores generated sequences on the basis of the observed pattern of labeled, extended oligos, as an indicator of oligo sequence present in the analyte.

The sequence-determination method may further include measuring the level of reporter in each array region of said pattern, and using the measured reporter level to determine the approximate length of oligo extension at each array position. This information may be used, for example, to refine the scoring in a genetic algorithm, for sequence determination.

One preferred assay format for carrying out the method is a capillary tube array, where each tube includes a different-sequence oligo carried on an inner wall portion of the tube.

These and other objects and features of the invention will become more fully apparent when the following detailed description of the invention is read in conjunction with the accompanying drawings.

BRIEF DESCRIPTION OF THE DRAWINGS

FIGS. 5A–5D illustrate successive nucleotide addition reactions suitable for stepwise synthesis of oligo probes having free 3' ends;

FIGS. 7A–7C illustrate how a pattern of extended oligos formed in accordance with the invention can be used to detect a point mutation in a portion of an analyte sequence.

DETAILED DESCRIPTION OF THE INVENTION

I. Definitions

Figure 1:
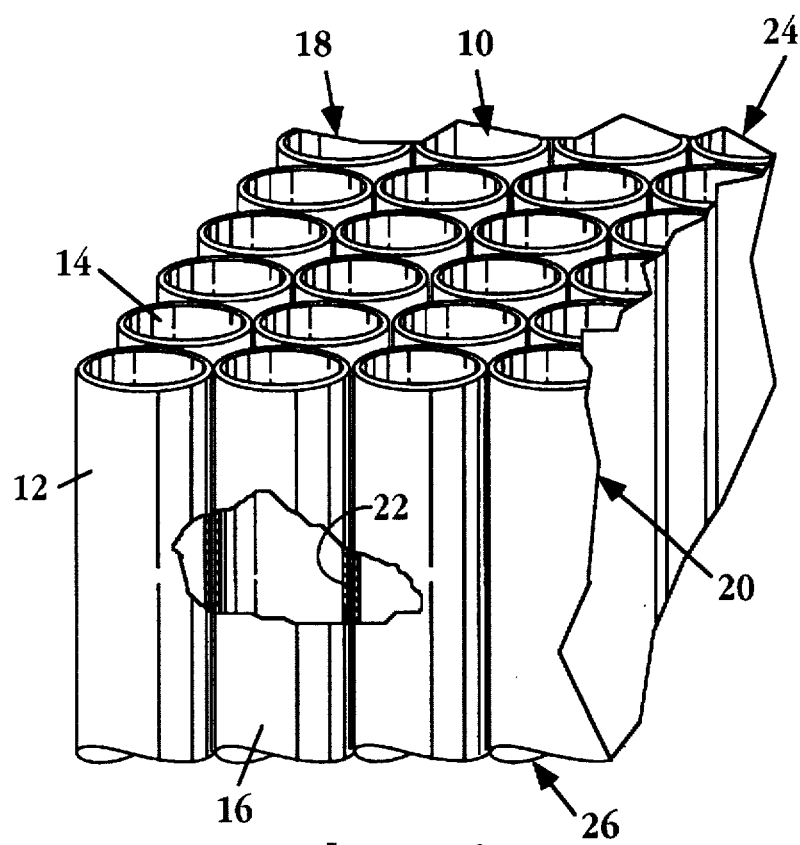
FIG. 1 is a fragmentary perspective view of a capillary-tube array used in forming an oligo combinatorial library array for use in practicing the invention.

The terms below have the following meanings, unless indicated otherwise:

"Oligonucleotides" or "oligos" refers to nucleotide oligomers nucleotides containing typically between about 3 and up to 50, and typically 5–15 nucleotide subunits. In the context of oligos attached at their 5' ends to an array support, in a position-addressable oligo array, the subunits forming the oligo may include or be composed primarily of nucleotide analog subunits, or other subunits capable of forming sequence-specific Watson-Crick base pairing, when assembled in a linear polymer, with the proviso that the free ends of the oligos are ribonucleotide or deoxyribonucleotide subunits capable of providing a suitable substrate for strand-directed polymerization in the presence of a DNA polymerase and one or more nucleotide triphosphates, e.g., conventional deoxyribonucleotides with free 3' OH groups.

A "known-sequence oligo" is an oligo whose base sequence in known.

A polynucleotide analyte is a nucleotide polymer having a length of typically 50 or more bases (i.e., subunits), and typically $10^2$–$10^7$ bases, and having at least a portion or region whose base sequence is to be determined or analyzed. The analyte may include, for example, a known-sequence polynucleotide having one or more point or localized mutations which are to be detected, or a polynucleotide whose entire base sequence, or a major portion thereof, is to be determined.

A "position-addressable array of different-sequence oligos" refers to a planar array of oligos, each oligo having a different, known, unique sequence associated with a known location (address) in the array.

A "combinatorial library of oligos" is a set of oligos containing substantially each sequence permutation that can be formed by placing a selected one of a number of different subunits at each of a selected number of residue positions. These residue positions may be contiguous or may be interrupted by one of more residues filled with a single subunit (or subunit sequence) only.

A "combinatorial sequence" refers to one of the possible permutation sequences in a combinatorial library of oligos.

"Complementary-strand hybridization conditions" refer to temperature, ionic strength and/or solvent conditions effective to produce sequence-specific hybridization between an single-stranded oligo and its complementary-sequence nucleic acid strand, for a given length oligo. Such conditions are preferably stringent enough to prevent or largely prevent hybridization of two nearly-complementary strands that have one or more internal base mismatches.

"Strand-directed polymerization" refers to nucleic acid strand extension, in the presence of a suitable DNA or RNA polymerase, and all four deoxynucleotide triphosphates, of primer strand hybridized to a template strand, where the sequence of bases in the template strand directs the sequence of bases added in the primer strand.

"Capillary tube" refers to any elongate tubular structure (i) whose cross section is, for example, a circular, elliptical, square, rectangular shape, (ii) which is preferably open at both ends (in an unplugged state), and (iii) whose cross-sectional area is sufficiently small to allthrough capillase in the tube through capillarity, i.e., surface tension.

II. Capillary Array Device

This section describes a capillary array device for producing a high-density array of combinatorial oligos, to use in practicing the present invention. The method employs a capillary tube array, such as array 10 shown fragmentarily in FIG. 1. The tubes in array 10, such as tubes 12, 14, and 16, are arranged in a planar array of N columns, such as column 18 containing tubes 12, 14, and M rows, such as row 20 containing tubes 12, 16. The array preferably includes at least $10^2$, more preferably at least $10^3$, and typically $10^4$ to $10^6$ tubes, in a square or rectangular array, such as where $M=N=10^2$ to $10^3$.

The tubes forming the array are conventional capillary tubes, such as are commonly used for capillary electrophoresis. Such tubes have an inner diameter of preferably between about 20–200 μm (microns), typically about 50 μm, and outer diameters that are 10–50 μm larger in diameter, i.e., with 5–25 μm wall thickness. For larger arrays, e.g., $10^4$ or larger, the tubes preferably have outer diameters of 100 μm of less. The tubes are cut or otherwise fashioned to lengths of preferably between 0.5 to 3 cm, typically about 1 cm. Each tube has a cylindrical inner wall portion, such as wall portion 22 in tube 16 (shown cutaway). It will be appreciated that a variety of tube cross-sectional shapes and areas, and tube lengths are suitable.

The two opposite tube ends regions of the array are referred to herein as first and second end regions 24, 26, respectively, which generally form top and bottom end regions the array, respectively. Unless otherwise indicated, each end region is meant to include the end region of each tube in the array; for example, end region 24 is meant to include the upper end region of each tube in the figure.

Where the method includes selective irradiation of a subset of tube ends in the array (as described below), the corresponding end regions of the tubes in the array are opaque with respect to adjacent tubes in the array. That is, light directed into the end region of any tube is blocked from entering the end region of adjacent tubes in the array. The tubes may be made opaque by a number of means: The tubes may be formed with an opacifying element or compound; the tubes may be coated or painted along their length or in an end region with an opaque coating material; or the array may be formed with an opaque matrix, e.g., and opaque polymer, that serves to hold the tubes in a rigid array, as well to optically isolate each tube in the array.

The array is formed by arranging the tubes in a desired, preferably close-packed array, as shown, and bonding the array tubes together in a suitable fashion. The bonding may be done, for example, with a suitable heat-adhesive coating applied to the outer tube walls, followed by heat curing or fixing of the formed array. Alternatively, the tubes may be embedded in a suitable matrix, e.g., an opaque polymer melt or solution, followed appropriate curing or polymerization to form a solid array block. The array block, once formed, may be cut at its upper and lower faces, if desired, to produce a uniform tube-end surface.

Figure 2:
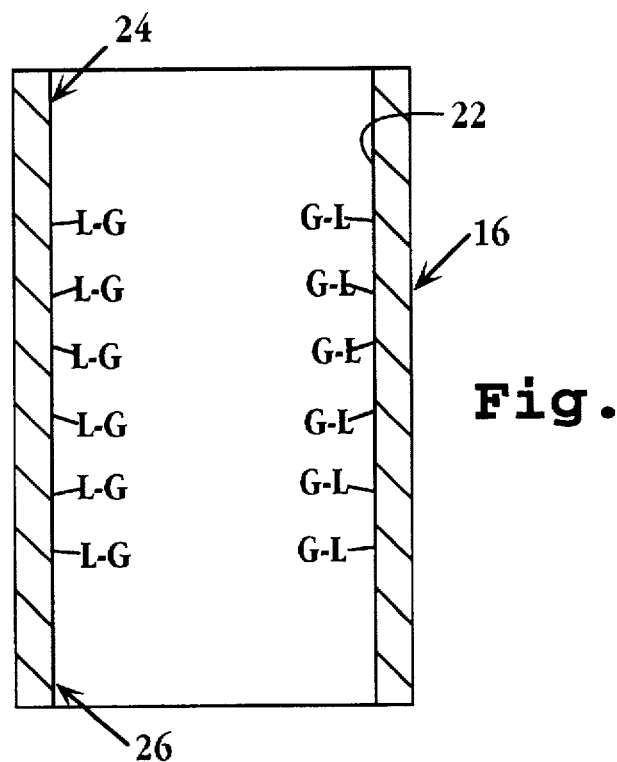
FIG. 2 is an enlarged sectional view of a capillary tube in a tube array, showing a central wall portion with attached linkers on which to build molecules of a library compound.

FIG. 2 is an enlarged section view of tube 16 in the array, showing inner wall portion 22 and upper and lower end regions 24, 26, respectively, in the tube. The glass tube has been treated conventionally in its central region to (i) form chemically reactive surface groups, such as carboxyl, hydroxyl, or amine groups on the inner wall portion, (ii) chemically link to the reactive groups, a linker L and a chemical group G which will serve as the chemical platform for solid-phase synthesis of the library compounds on the wall portions of the tubes. Methods for derivatizing glass surfaces for a various types of solid-phase synthesis are well known, e.g., U.S. Pat. Nos. 5,436,327, 5,142,047, 5,137,765, and 4,992,383. Suitable linkers terminating in reactive chemical groups are also well known, and are exemplified below.

III. Oligo Library Production Method

This section describes the use of the above device for the construction of a position-addressable library of oligos. In particular, the method will be illustrated for the synthesis of an oligo library having every combination of four nucleosides subunits, e.g., deoxyadenosine (A), deoxyguanosine (G), deoxycytidine (C), and deoxythymidine (T), in a library of octanucleotides, i.e., $4^8=65,536$ different-sequence oligos. In this case, the tube array will include at least $4^8$ tubes, e.g., in a 256×256 array.

At each subunit addition step, the array is divided into four subsets, each containing at least 16,384 tubes, and each intended for subunit addition of one of the four nucleotide bases. For example, at the first subunit addition step, the array may be divided into four 128×128 quadrants, one for each different nucleotide in the first oligomer position. Each of these quadrants represents a selected subset, with the remaining tubes in the array, e.g., the remaining 49,152 tubes in the array representing a complementary subset.

As will be detailed below with reference to FIGS. 3A–3E, the method involves selectively exposing the tubes in each selected subset to a reaction reagent containing one of the four nucleotides, to add that nucleotide to the oligomer being formed on the wall portion in each tube of that subset. Thus, in the case where each subset is one quadrant of the tube array, a reagent solution containing one of the four nucleotides is added selectively to all of the tubes in one of the quadrants, and the solution is allowed to react with the wall portions in those tubes until the nucleotide has been added to the growing oligomer attached to the wall portion. Thereafter, solutions containing each of the other three nucleotides are added successively to the tubes in each of the other three quadrant subsets.

At the second subunit-addition step, each of the first quadrants may be divided into four 64×64 subquadrants, one for each different base. In this case, the subset of tubes for each different nucleotide is composed of four 64×64 subquadrants, one in each quadrant, and the complementary subset of remaining tubes is composed of the other three subquadrants in each of the four original quadrants. For this subunit addition, reagent solution for each nucleotide base is added successively to each of these four subsets, i.e., in four successive nucleotide addition reactions. As above, and in accordance with the invention, reagent solution is drawn into all of the tubes in each subset, so that only four solution additions are required to complete subunit addition at each of oligo residue position.

Similarly, at the third subunit addition step, each of the just-mentioned subquadrants is further divided into four equal size (32×32) subquadrants, with each nucleotide subset now being composed of sixteen 32×32 subquadrants. Again reagent solution for each of the four nucleotides is drawn into all of the tubes in the sixteen separate subarrays, so that all four nucleotides can be added with four solution additions.

Figure 3A:
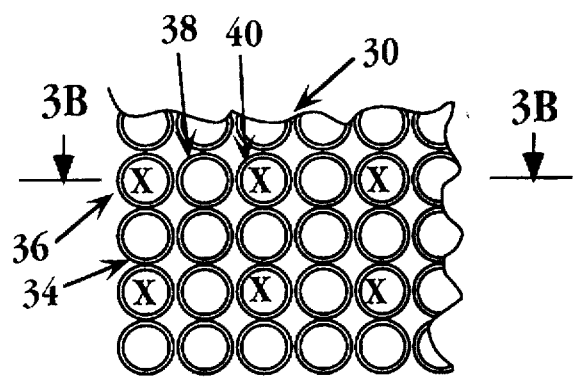
FIGS. 3A–3E illustrate successive steps for introducing a reagent solution into the tubes in a selected subset of tubes in a capillary tube array, where selective irradiation of tubes in the array is carried out by photomasking.

This process is repeated until at the final oligo position, each of the penultimate quadrants, containing 4 members each, is divided into four tubes, such that the subsets for A, G, C, and T addition now each include 16,364 spatially separated tubes, each tube being part of a four-tube subarray. The latter configuration of subsets is illustrated in FIG. 3A, which shows a plan view of a portion of a capillary tube array 30 used in the construction of the above oligo library. Here a selected position, such as the position indicated by "X" in the figure, in each 2×2 group of four tubes, such as the group indicated at 34, is assigned to one of the four nucleotide bases, i.e., A, G, C, or T, with each defined-position tube in all 16,384 2×2 groups representing one of the four subsets in the array.

To selectively add reagent solution to one of the subsets, e.g., those corresponding to position "X" in the figure, the tubes in the complementary subset, i.e., the tubes in the remaining three subsets, are selectively blocked at one end region, typically the upper end region of the tubes. The array is then placed in contact with the selected reagent solution, typically by immersing the opposite tubes ends of the array in the solution, wherein solution is drawn by capillarity into the tubes in the selected subset, but blocked from entering the tubes in the complementary subset. The solution in the selected-subset tubes is allowed to react with the growing oligomer on the tubes' wall portions until the subunit in the solution has been added to the oligomer end.

Figure 3B:
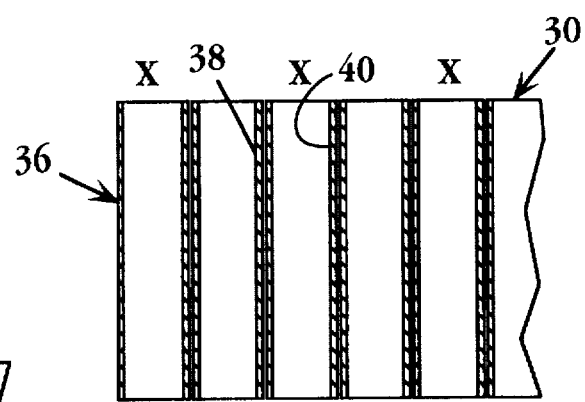

FIGS. 3B–3E illustrate one preferred method for drawing reagent solution into the tubes in a selected subset in the array. FIG. 3B shows a sectional view of a row 36 of tubes, such as tubes 38, 40, taken along section line 3B—3B in FIG. 3A. As described above, it is desired to draw reagent solution for a selected nucleotide into each of 16,384 tubes in a given subset, which is here a subset defined by one of the four positions, such as position "X", in each of the 16,384 groups of four tubes in the array. The tubes in row 36, such as tube 40, into which reagent solution is to be drawn, are indicated with an "X", as in FIG. 3A. Tubes in the complementary subset, such as tube 38, are intended not to be exposed to the such reagent solution.

Figure 3C:
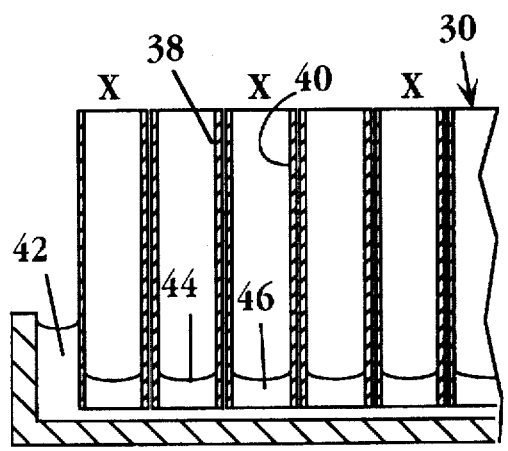

Initially, and with reference to FIG. 3C, one end of the array, e.g., the lower end, is immersed in a solution of a radiation-polymerizable polymer, indicated at 42 in FIG. 3C. As shown, the array is contacted with the polymer solution under conditions sufficient to draw solution into an end region of the tubes in the array, typically to a level in which the solution fills at least 5–10% of the total tube volume. The polymer solution in tubes 38, 40 is indicated at 44, 46, respectively. One exemplary solution is a 3–20 w/v % acrylamide/bisacrylamide solution containing persulfate and TEMED (N,N,N',N'-tetramethyethylene diamine) as light-sensitive initiators, such as is commonly used for acrylamide gel electrophoresis (see, for example, Sambrook, 6.36–6.62). More generally, the polymer solution is one capable of being drawn by capillarity into the tubes, and capable of forming a non-flowable plug upon exposure to radiation, such as UV, visible, or infrared light.

Figure 3D:
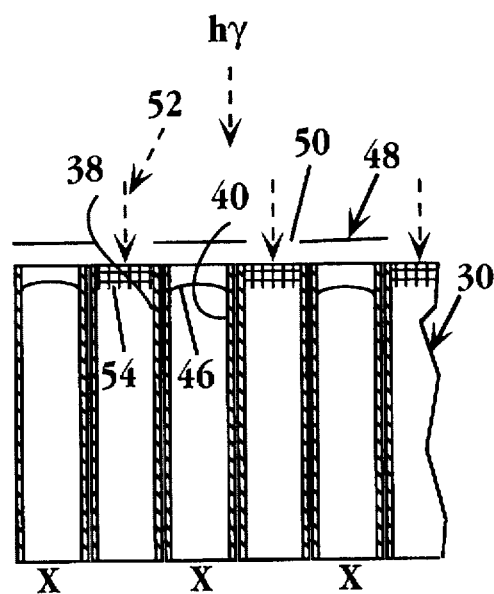

FIG. 3D illustrates one method for selectively polymerizing polymer solution in the end regions of the tubes in the complementary subset in the array. Here array 30 is inverted and placed below a photomask 48 having a pattern of holes, such as hole 50, corresponding to the tubes in the array in the complementary subset, i.e., the tubes into which reagent solution is to be blocked. Methods of forming photomasks with a desired pattern of holes are well known, e.g., U.S. Pat. Nos. 5,429,896, 5,217,829 and 4,981,765.

The tubes are irradiated through the photomask by a suitable wavelength beam 52, such as a visible light beam in the case of the above acrylamide/bisacrylamide solution, selectively irradiating those tube ends in the complementary subset of tubes, as indicated. Irradiation is carried out until a suitable degree of polymer polymerization and/or crosslinking is achieved, that is, until a non-flowable polymer plug forms in the irradiated tube ends, such as non-flowable plug 54 in tube 38. As indicated above, the end regions of the tubes are opacified to confine radiation-induced polymerization to the irradiated tubes only. At this point, the array end containing the polymer plugs may be blotted to draw polymer solution out of the non-irradiated tubes.

Figure 3E:
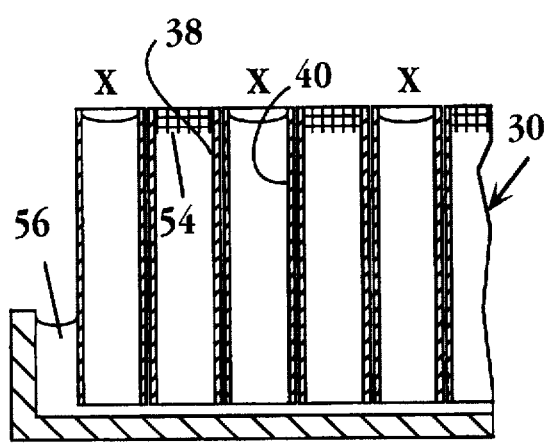

Following the selective blocking of tubes in the complementary array, the ends of the array tubes, and typically the ends opposite the plugged ends, are placed in contact with the selected reagent solution, such as solution 54 in FIG. 3E. The reagent solution contains the component(s) necessary for the chemical reaction that will add a selected subunit or substituent to the library compound being formed on the tube wall portions, as described below for oligo, oligopeptide, and a small-molecule library synthesis. One of more of the chemically reactive components in the solution may be carried on a solid-phase bead particle or the like.

When the array is placed in contact with the reagent solution, as illustrated in FIG. 3E, the solution is drawn into the unplugged selected-subset tubes, such as tube 40, by capillarity, but blocked from being drawn into the plugged tubes, such as tube 38, in the complementary-subset tubes. The solution is allowed to react with the wall portions of the selected-subset tubes until the subunit or substituent addition reaction (see below) is essentially complete. Thereafter, the solution is removed from the tubes, e.g., by blotting or by applying negative gas pressure across the tube ends. The array is also treated, e.g., by negative pressure across the tubes, to remove the polymer plugs.

The array is now ready for another reagent reaction, in which a selected reagent solution is drawn into another subset of array tubes, following the steps just detailed, but for another tube subset.

Figure 4:
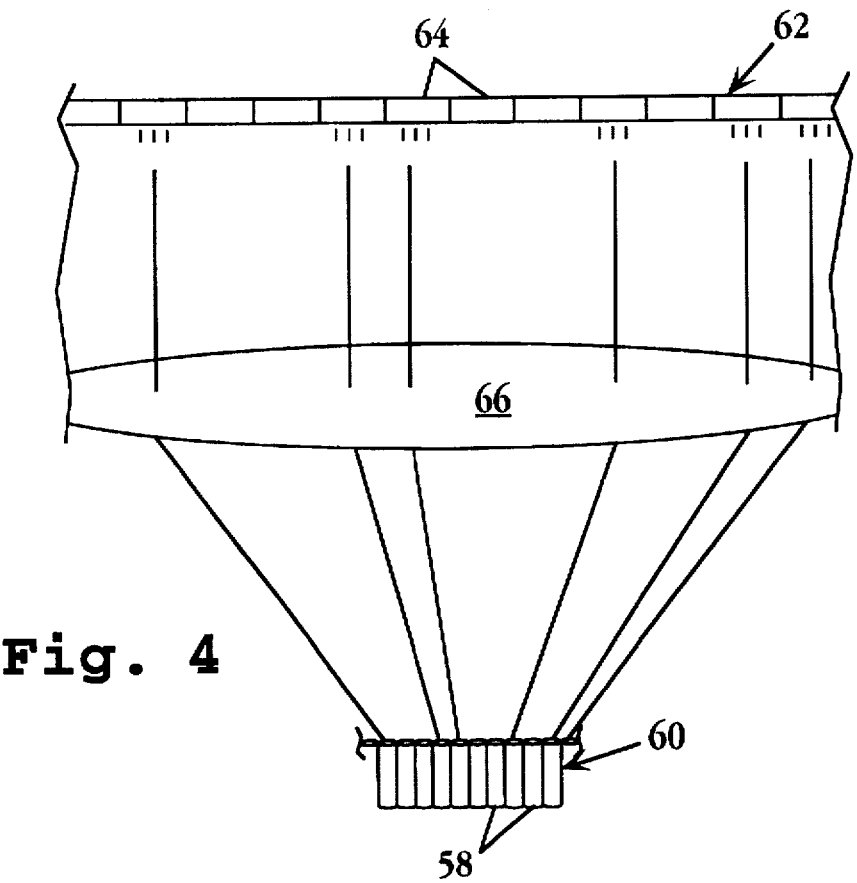
FIG. 4 illustrates a method for selectively irradiating tubes in a capillary tube array by means of a focused light-emitting diode array.

FIG. 4 illustrates another method of selectively irradiating the ends of capillary tubes in a selected subset tubes, such as tubes 58, in a tube array 60, where the polymer solution can be photopolymerized. Here the visible light source is a planar array 62 of light emitting diodes (LED's), such as those represented at 64. Each LED can be switched between off on light-emitting conditions, to form a pattern of light-emissions corresponding to the planar pattern of the complementary tube-array subset whose tube ends are to be blocked. Light-emitting diode arrays suitable for this purpose are well-known, e.g., as described in U.S. Pat. No. 5,449,926.

The pattern of light emissions from array 62 is focused by a condensing lens or lens system, indicated at 66, producing at a focal plane corresponding to the upper surface of the array, a pattern of light beams that is in registry with the pattern of tubes in the selected complementary subset of array tubes, as indicated. An advantage of the LED configuration is that desired light-array patterns needed for the several different subsets used during library production can be quickly and inexpensively generated.

In another general embodiment, the array may be processed to selectively block tubes in the complementary subset of tubes by selectively photoablating a film covering the tubes ends at one array end. The film may be, for example, a thin wax or polymer film that is placed over the tube ends in a sealing fashion. The film is then selectively photoablated, e.g., by a focused laser beam rastered over the array, at positions corresponding to ends of tubes in the selected subset, to "open" the film at these tube ends.

IV. Oligo Library

FIGS. 5A–5C illustrate an exemplary synthetic scheme used for preparation of the library of oligos on the wall portions of glass tubes, in accordance with the invention. In these figures, a portion of a capillary-tube glass wall is indicated at 70, which is derivatized, conventionally, with a linker 72, to which the first nucleotide subunit (or a pre-library subunit) is then attached via its 5' OH end. The linker molecules are preferably of sufficient length to permit the compounds in the completed library device to interact freely with probe sequences to which the device is exposed in forming the probe array of Section III. Longer linkers are also known to lead to more efficient nucleoside coupling reactions (Gait, p. 45).

The linkage in the present example may be formed by (i) reacting the glass tube, which may be derivatized to contain amine or carboxyl groups, if desired, with a long chain bifunctional reagent such as a diol, diamine, ethylene glycol oligomer or amine-terminated ethylene glycol oligomer; and (ii) reaction of the free hydroxyl or amino end of the linker with the first nucleoside (or a pre-library nucleotide or sequence), whose 5'-hydroxyl has been converted to a suitable leaving group such as a mesylate, and which is protected in its 3' position with a suitable protecting group, e.g., phenoxyacetyl (Pac) (Virnekas) and also base-protected. After coupling to the linker, the 3' OH group of the newly added nucleotide is then deprotected, e.g., by reaction with $NH_3$ in MeOH, and activated with $MeOP(N^iPr_2)Cl$ in $EtN^iPr_2$, using standard procedures (Virnekas), and as illustrated in FIGS. 5A and 5B.

The phosphotriester will be converted to a phosphate linkage after oligo synthesis is complete. Also, the substrate-to-oligo linkage is base stable, and the oligos will thus remain bound to the substrate throughout the deprotection steps which conclude the synthesis. This issue has been addressed by Southern and Matson, inter alia.

After 3'-deprotection and activation at the 3' OH group, a second 3'-protected nucleoside (e.g., deoxyguanosine) is added, giving the dimer AG sequence (FIG. 5C) after oxidation. These steps are repeated with further nucleoside units (FIGS. 5C and 5D) until the desired oligos have been formed on the filament. At this point, the terminal 3'-hydroxy groups are deprotected, and activated, as above, except that the terminal nucleotide is left in a free 3'-OH form. Finally, the methyl groups on the phosphotriester linkages are removed by treatment with thiophenol or ammonia, and the purine and pyrimidine bases are deprotected, e.g., by treatment with ammonia, all according to known methods (e.g., Gait).

Each nucleoside added in the synthesis is 3'-protected, preferably by a phenoxyacetyl (Pac) group. The exocyclic amino groups on the purine and pyrimidine bases of the nucleosides are also protected, as amides, throughout the sequence, according to well established methods (Gait), and can be deprotected by treatment with ammonia upon completion of the library synthesis. Because the coupling reactions are sensitive to air and moisture, they are preferably carried out under an inert atmosphere.

The members of the oligo library illustrated above consist of a sequence of single deoxyribonucleotides. Alternatively, the subunits forming the library may be dinucleotides, trinucleotides, or higher order oligos. For example, at each subunit addition step, one of typically 2–5 different trinucleotide "subunits" corresponding to one of up to amino acid codons, could be added at each subunit addition step (Virnekas).

The oligos on the array are preferably 6–25, more preferably 8–12 single-nucleotides subunits in length.

Other solid supports for an oligo library, such as the filament and planar array supports described in co-pending U.S. patent application for "Position-Addressable Polynucleotide Arrays" are also suitable.

V. Method of Analyzing Polynucleotide Analytes

The invention employs a position-addressable array of oligos, such as the array described above, for analyzing a polynucleotide analyte. The analyte may be a known-sequence gene or other genetic regions, e.g., regulatory region, having one or a number of possible mutations, where the method is designed to detect the presence or absence of particular mutation(s). Alternatively, the analyte may have an unknown sequence, at least in one or more regions, where the method is designed to determine the unknown sequence.

VI. Forming Labeled, Extended Oligos

Figure 6B:
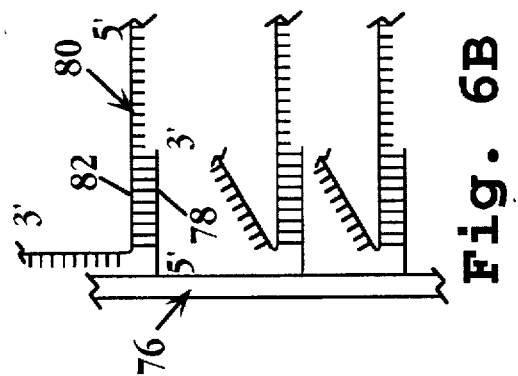
FIGS. 6A–6D illustrate successive steps in polynucleotide analyte extension on a selected array probe, in accordance with the invention.
Figure 6A:
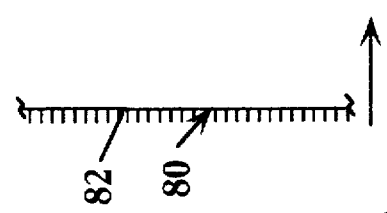
Figure 6A:
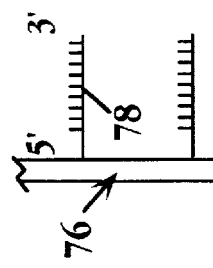

In practicing the method, the analyte is contacted with a position-addressable array of oligos of the type described above, where each oligo is anchored to a solid support and has a 5'-proximal and 3'-distal orientation. FIG. 6A shows a portion of a glass tube in 76 in a capillary-tube oligo array of the type described above. The single-stranded oligo molecules on the inner tube wall, such as oligo 78, have a unique permutation sequence associated with that tube, also as described above, where the tick marks on the molecules represent the bases (in this case, 9 bases) forming the sequence.

The analyte is preferably brought into contact with the entire oligo array at once. In the case of a capillary-tube array, this is done by allowing a solution of analyte to be drawn into all of the tubes of the array by capillarity. The analyte is contacted with the oligos under conditions that allow hybridization of the analyte, with such in single-stranded form, to array oligos whose sequences are complementary to sequences within the analyte. More specifically, the conditions are selected to favor hybridization between the array oligos and complementary-sequence regions of the analyte. The hybridization conditions are preferably stringent (high-criterion) conditions in which only hybrids with a high degree of complementarity form. Typical high criterion conditions are about 8° C. lower than the melting temperature $T_m$ (Hames, p. 108). Thus, for example, in the case of 9 mer hybrids, where a melt temperature of about 40° C. may be expected, a high-criterion annealing or hybridization temperature may be about 32° C.

In the figures, the analyte, such as the analyte molecule indicated at 80, includes a 9 mer region 82 that is complementary in its base sequence to the base sequence of oligo 78; that is, the two complementary regions form a Watson- Crick base-paired duplex structure, as indicated in FIG. 12, under the selected hybridization conditions.

Figure 6C:
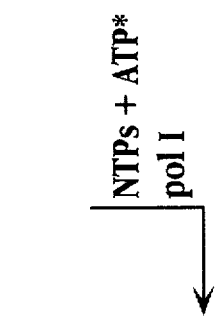
Figure 6C:
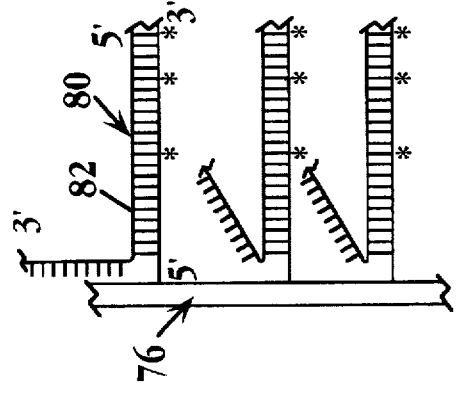

The oligos attached to the array are now extended by strand-directed polymerization along the analyte segments that extend beyond the 3' ends of the hybridized oligo. That is, the oligos are extended to the 5' ends of the analyte molecules, using the analyte molecules as templates, yielding extended duplex structures between the extended oligos, such as extended oligo 82 in FIG. 6C, and the 5'end portion of the analyte, as illustrated in FIG. 6C.

The polymerization reaction may be carried out in the presence of a reporter-labeled nucleotide triphosphate, such as indicated by *ATP, that is readily incorporated into newly synthesized DNA. The nucleotide may be labeled with a ligand, such as biotin or an antigen, that can react with a secondary reporter, such as fluorescent-labeled antibody, in the case of an antigen ligand, or fluorescent-labeled avidin or streptavidin in the case of biotin. As indicated in FIG. 6C, the labeled nucleotide becomes incorporated into the extended oligo, at positions corresponding to the appropriate base. Alternatively, the extended oligo, with such in the duplex form indicated in FIG. 6C may be labeled with a detectable duplex intercalating agent, such as ethidium bromide, employing established methods.

Suitable polymerization conditions in the presence of a DNA polymerase, e.g., Klenow fragment of *E. coli* DNA polymerase I, T4 DNA polymerase, T7 polymerase, and all four nucleotide triphosphates (NTP's), are well known (e.g., Sambrook, 5.35–5.51).

Figure 6D:
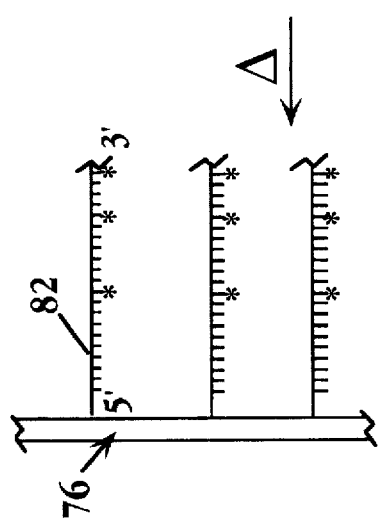

As a final step in the biochemical steps in the method, the capillary array may be washed, e.g., by drawing washing solution in and out of the capillary tubes, to remove unbound or unincorporated label. Where the extended oligos include labeled nucleotide subunits, the washing may further include a heat or solvent-denaturation step, to remove unlabeled analyte strand, as indicated in FIG. 6D.

The pattern of reporter label in the array may be generated by known methods, such as described in co-pending patent application for "Method and Apparatus for Producing Position-Addressable Combinatorial Libraries". Briefly, a fluorescence reader for a planar or capillary-tube array may include a laser beam at a fluorescence excitation wavelength, a stage for relatively moving the beam and array in an x-y plane, and a photodetector for measuring emitted fluorescence light, as a function of state position.

Alternatively, for detection of fluorescent labeled extended oligos in a capillary tube array, the array may be irradiated at its upper side by a broad beam of light at the fluorescence emission wavelength, and the pattern of emitted light at the other ends detected by a CCD array device or film or other detection device, through suitable filters to remove excitation wavelength light.

A. Analysis of Local Sequence

In one general embodiment of the invention, the method is used to detect local sequence changes, e.g., point or other small mutations, or sequence deletions or insertions, in a polynucleotide analyte. Typically, the analyte will be a gene whose sequence is known, where one or more mutated forms of the gene are also known. A well-known example is the cystic fibrosis gene in which a large number of different local mutations have been described.

In practicing this embodiment of the method, the analyte is hybridized to the oligo array, and the hybridized oligos are extended by strand-directed polymerization and labeled, as above. For any given analyte sequence, a pattern of labeled array elements can be constructed from the expected hybridization pattern of the sequence to the array oligos. To illustrate, FIG. 7A shows a portion of a sequence in one strand of a wildtype analyte polynucleotide. The mutation of interest, for purposes of sequence analysis, is a T to G mutation at the position shown in the figure.

To generate a pattern of expected extended oligos for the wildtype and mutated forms of the gene, all of the oligos in a given-length oligo array which can hybridize with a complementary region of the analyte are determined. As an example, FIG. 7B shows all of the 8 mer oligos that will hybridize to the portion of the wildtype sequence shown in FIG. 7A. Thus, each of the array positions containing these oligos will "light up", i.e., have labeled extended nucleotides.

FIG. 7C shows the oligos that will hybridize with the same gene analyte region, but where the gene contains the T to G mutation indicated. For oligos 8 or more base positions away form the site of the mutation, the pattern of extended oligos will be the same as for wildtype. For those oligos that are seven base positions or less from the mutation site, the pattern of extended oligos will correspond to those shown in bold in FIG. 3C. The array pattern involving the latter oligos will thus be characteristic of an analyte having a T to G mutation at the site indicated.

It will be appreciated how other types of mutations, including insertion and deletion mutations, can be similarly detected in accordance with the invention.

A. Sequencing by Hybridization

In another aspect, the method is designed for determining the base sequence of an analyte whose base sequence is unknown, at least in large regions of the analyte.

The general methodology for sequencing by hybridization (SBH) to a permutation library of fixed-length oligos has been described (e.g., Southern, Khrapko, Drmanac, Fodor). Briefly, the method involves first identifying oligos in an oligo permutation library that bind to the analyte. The sequences of the binding oligos are then reconstructed, by sequence overlap construction, to determine a full analyte sequence.

To date, this method has been applied successfully to determination of short sequences, but tends to lead to sequence ambiguities for longer sequences, e.g., 100 Kb or larger. One reason for the sequence ambiguity is duplicated short sequences in the analyte, which can lead to unresolved sequence determination. Although in theory this problem can be solved by generating longer-sequence oligo libraries, this solution requires a much larger and more complex permutation library. It also increases the likelihood of single-mismatch hybridization, since longer stretches of duplex will accommodate more basepair mismatching, even under high stringency conditions, especially in duplex regions with high GC content.

The present invention solves these problems by a different approach. In essence, the method uses information from the oligo array pattern to construct a first approximation to a sequence, employing conventional methods of sequence reconstruction by oligo-sequence overlap. This sequence is then refined using data relating to the positions of the oligo sequences along the length of the analyte. The position data is obtained by determining the level of reporter signal at each region of extended oligo. A higher level of signal means that a relatively large portion of the analyte sequence has been copied, in oligo extension, indicating that the particular oligo sequence in the analyte is located closer to the 3' end the analyte. Similarly, a lower level of labeling, or signal, means that the analyte portion copied is relatively short, and thus located near the analyte strand's 5' end.

The level of signal may also be reduced in cases of sequence mismatch between oligo and analyte sequence, in that strand-directed polymerization may be less efficient and/or a relatively low percentage of analyte molecules may be bound to the oligos. To discriminate between low labeling due to relatively short segments of analyte, and relatively inefficient copying, the labeling levels of analyte hybridized under highly stringent conditions and under less stringent conditions can be compared. Where a significant difference in labeling levels is observed between the high and low stringency conditions, a low labeling level (which would be favored by high stringency conditions) would then indicate a basepair mismatch between oligo and analyte sequence, and that oligo sequence could be ignored as representing basepair mismatch.

As indicated above, labeling level data related to sequence position in the analyte is used to generate a refined analyte sequence. This may be done, for example, using known genetic algorithm methods in which a number starting sequences (e.g., those generated from array-pattern data alone) are subjected to successive crossovers, to generate new sequences that are then evaluated for fitness in terms of the array-pattern sequence and the analyte-position data, with the top scoring sequences being used for further sequence generation. The rounds of replication are allowed to continue until sequence convergence to a optimal score or scores is achieved.

Although the invention has been described with respect to particular methods and library arrays, it will be appreciated that various changes and modification can be made without departing from the invention.

It is claimed:

1. A method of analyzing a polynucleotide analyte sequence, comprising (i) contacting the analyte with a position-addressable array of oligonucleotides formed in an array of capillary tubes, where each capillary tube in the tube array includes a different-sequence oligonucleotide attached to an inner wall portion of that tube and having a 5'-proximal and 3'-distal orientation, said contacting being carried out under conditions that allow hybridization of the analyte, wherein said analyte is in single-stranded form, to array oligonucleotides whose sequences are complementary to sequences within the analyte, (ii) extending analyte-hybridized array oligonucleotides by strand-directed polymerization, along analyte segments extending distal to the 3' ends of the hybridized array oligonucleotides, to produce extended oligonucleotides, (iii) during or after said extending, labeling the extended oligonucleotides with a detectable reporter, and (iv) analyzing the analyte sequence from the observed pattern of labeled, extended oligonucleotides in the array.

2. The method of claim 1, wherein said labeling includes adding ethidium bromide to the extended oligonucleotides, with such in a double-stranded form.

3. The method of claim 1, wherein said labeling includes incorporating a reporter-labeled nucleotide into said extended oligonucleotides during said extending.

4. The method of claim 3, wherein said reporter-labeled nucleotide is a biotinylated nucleotide, and said labeling further includes adding a reporter-labeled avidin or streptavidin reagent to the extended oligonucleotides.

5. The method of claim 3, wherein said reporter-labeled nucleotide is a fluorescent-labeled nucleotide.

6. The method of claim 6, wherein the analyte-hybridized array oligonucleotides are extended with fluorescent label, and said analyzing includes measuring the level of fluorescence of emission associated with different extended oligonucleotides in the array.

7. The method of claim 1, for use in analyzing the presence or absence of a sequence mutation at a given position in the analyte, wherein said analyzing includes comparing the observed pattern of extended oligonucleotides in the array with that expected for an analyte sequence having a known sequence at the position of the mutation.

* * * * *